US012733847B2

(12) United States Patent
Iyengar et al.

(10) Patent No.: US 12,733,847 B2
(45) Date of Patent: Sep. 15, 2026

(54) PHYSIOLOGICAL MEASUREMENT CALIBRATION

(71) Applicant: Masimo Corporation, Irvine, CA (US)

(72) Inventors: Prashanth Iyengar, Irvine, CA (US); Jerome Novak, Aliso Viejo, CA (US); Prashanth Rengaswamy Chandran, Irvine, CA (US)

(73) Assignee: Masimo Corporation, Irvine, CA (US)

(*) Notice: Subject to any disclaimer, the term of this patent is extended or adjusted under 35 U.S.C. 154(b) by 0 days.

(21) Appl. No.: 18/750,781

(22) Filed: Jun. 21, 2024

(65) Prior Publication Data

US 2024/0341646 A1 Oct. 17, 2024

Related U.S. Application Data

(63) Continuation of application No. 17/061,945, filed on Oct. 2, 2020, now Pat. No. 12,042,285, which is a continuation of application No. 15/499,806, filed on Apr. 27, 2017, now Pat. No. 10,827,961, which is a continuation of application No. 14/160,322, filed on Jan. 21, 2014, now abandoned, which is a continuation-in-part of application No. 14/011,567, filed on Aug. 27, 2013, now abandoned.

(60) Provisional application No. 61/713,833, filed on Oct. 15, 2012, provisional application No. 61/694,723, filed on Aug. 29, 2012.

(51) Int. Cl.

| | |
|---|---|
| ***A61B 5/1495*** | (2006.01) |
| ***A61B 5/00*** | (2006.01) |
| ***A61B 5/026*** | (2006.01) |
| ***A61B 5/145*** | (2006.01) |
| ***A61B 5/1455*** | (2006.01) |
| ***A61B 5/1491*** | (2006.01) |

(52) U.S. Cl.
CPC ............ *A61B 5/1495* (2013.01); *A61B 5/026* (2013.01); *A61B 5/14546* (2013.01); *A61B 5/1455* (2013.01); *A61B 5/1491* (2013.01); *A61B 5/7246* (2013.01); *A61B 2562/0238* (2013.01); *A61B 2562/04* (2013.01)

(58) Field of Classification Search
CPC ... A61B 5/1495; A61B 5/026; A61B 5/14546; A61B 5/1455; A61B 5/1491; A61B 5/7246; A61B 2562/0238; A61B 2562/04
See application file for complete search history.

(56) References Cited

U.S. PATENT DOCUMENTS 4,869,253 A 9/1989 Craig, Jr. et al.
4,960,128 A 10/1990 Gordon et al.
(Continued)

FOREIGN PATENT DOCUMENTS

WO WO 03/039326 5/2003

OTHER PUBLICATIONS

US 2022/0192529 A1, 06/2022, Al-Ali et al. (withdrawn)
US 2024/0016391 A1, 01/2024, Lapotko et al. (withdrawn)

*Primary Examiner* — Abid A Mustansir
(74) *Attorney, Agent, or Firm* — Knobbe, Martens, Olson & Bear, LLP

(57) ABSTRACT

The present disclosure provides a calibration system and method for calibrating a physiological measurement based on a variable that affects the measurement. The variable can be a related physiological measurement. The technique can be implemented to obtain robust calibrations with minimal test data and computational effort.

19 Claims, 4 Drawing Sheets

(56) References Cited

U.S. PATENT DOCUMENTS

| | | | |
|---|---|---|---|
| 4,964,408 | A | 10/1990 | Hink et al. |
| 5,041,187 | A | 8/1991 | Hink et al. |
| 5,069,213 | A | 12/1991 | Hink et al. |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| 5,377,676 | A | 1/1995 | Vari et al. |
| 5,431,170 | A | 7/1995 | Mathews |
| 5,436,499 | A | 7/1995 | Namavar et al. |
| 5,452,717 | A | 9/1995 | Branigan et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |
| 5,692,503 | A | 12/1997 | Kuenstner |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,438,399 | B1 | 8/2002 | Kurth |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,738,652 | B2 | 5/2004 | Mattu et al. |
| 6,745,060 | B2 | 6/2004 | Diab et al. |
| 6,760,607 | B2 | 7/2004 | Al-Ali |
| 6,770,028 | B1 | 8/2004 | Ali et al. |

(56) References Cited

U.S. PATENT DOCUMENTS

| | | | |
|---|---|---|---|
| 6,771,994 | B2 | 8/2004 | Kiani et al. |
| 6,788,965 | B2 | 9/2004 | Ruchti et al. |
| 6,792,300 | B1 | 9/2004 | Diab et al. |
| 6,813,511 | B2 | 11/2004 | Diab et al. |
| 6,816,241 | B2 | 11/2004 | Grubisic |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,876,931 | B2 | 4/2005 | Lorenz et al. |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin IV |
| 6,950,687 | B2 | 9/2005 | Al-Ali |
| 6,956,649 | B2 | 10/2005 | Acosta et al. |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,990,364 | B2 | 1/2006 | Ruchti et al. |
| 6,993,371 | B2 | 1/2006 | Kiani et al. |
| 6,996,427 | B2 | 2/2006 | Ali et al. |
| 6,998,247 | B2 | 2/2006 | Monfre et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,048,687 | B1 | 5/2006 | Reuss et al. |
| 7,067,893 | B2 | 6/2006 | Mills et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,132,641 | B2 | 11/2006 | Schulz et al. |
| 7,133,710 | B2 | 11/2006 | Acosta et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Ai-Ali |
| 7,215,984 | B2 | 5/2007 | Diab et al. |
| 7,215,986 | B2 | 5/2007 | Diab et al. |
| 7,221,971 | B2 | 5/2007 | Diab et al. |
| 7,225,006 | B2 | 5/2007 | Al-Ali et al. |
| 7,225,007 | B2 | 5/2007 | Al-Ali et al. |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali et al. |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al-Ali et al. |
| 7,377,899 | B2 | 5/2008 | Weber et al. |
| 7,383,070 | B2 | 6/2008 | Diab et al. |
| 7,395,158 | B2 | 7/2008 | Monfre et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty et al. |
| 7,620,674 | B2 | 11/2009 | Ruchti et al. |
| D606,659 | S | 12/2009 | Kiani et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,904,132 | B2 | 3/2011 | Weber et al. |
| 7,909,772 | B2 | 3/2011 | Popov et al. |
| 7,910,875 | B2 | 3/2011 | Al-Ali |

(56) References Cited

U.S. PATENT DOCUMENTS

| | | | |
|---|---|---|---|
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Ai-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,280,473 | B2 | 10/2012 | Ai-Ali |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |

(56) References Cited

U.S. PATENT DOCUMENTS 8,781,543 B2 7/2014 Diab et al.
8,781,544 B2 7/2014 Al-Ali et al.
8,781,549 B2 7/2014 Al-Ali et al.
8,788,003 B2 7/2014 Schurman et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,831,700 B2 9/2014 Schurman et al.
8,840,549 B2 9/2014 Al-Ali et al.
8,847,740 B2 9/2014 Kiani et al.
8,849,365 B2 9/2014 Smith et al.
8,852,094 B2 10/2014 Al-Ali et al.
8,852,994 B2 10/2014 Wojtczuk et al.
8,868,147 B2 10/2014 Stippick et al.
8,868,150 B2 10/2014 Al-Ali et al.
8,870,792 B2 10/2014 Al-Ali et al.
8,886,271 B2 11/2014 Kiani et al.
8,888,539 B2 11/2014 Al-Ali et al.
8,888,708 B2 11/2014 Diab et al.
8,892,180 B2 11/2014 Weber et al.
8,897,847 B2 11/2014 Al-Ali
8,909,310 B2 12/2014 Lamego et al.
8,911,377 B2 12/2014 Al-Ali
8,912,909 B2 12/2014 Al-Ali et al.
8,920,317 B2 12/2014 Al-Ali et al.
8,921,699 B2 12/2014 Al-Ali et al.
8,922,382 B2 12/2014 Al-Ali et al.
8,929,964 B2 1/2015 Al-Ali et al.
8,942,777 B2 1/2015 Diab et al.
8,948,834 B2 2/2015 Diab et al.
8,948,835 B2 2/2015 Diab
8,965,471 B2 2/2015 Lamego
8,983,564 B2 3/2015 Al-Ali
8,989,831 B2 3/2015 Al-Ali et al.
8,996,085 B2 3/2015 Kiani et al.
8,998,809 B2 4/2015 Kiani
9,028,429 B2 5/2015 Telfort et al.
9,037,207 B2 5/2015 Al-Ali et al.
9,060,721 B2 6/2015 Reichgott et al.
9,066,666 B2 6/2015 Kiani
9,066,680 B1 6/2015 Al-Ali et al.
9,072,474 B2 7/2015 Al-Ali et al.
9,078,560 B2 7/2015 Schurman et al.
9,084,569 B2 7/2015 Weber et al.
9,095,316 B2 8/2015 Welch et al.
9,106,038 B2 8/2015 Telfort et al.
9,107,625 B2 8/2015 Telfort et al.
9,107,626 B2 8/2015 Al-Ali et al.
9,113,831 B2 8/2015 Al-Ali
9,113,832 B2 8/2015 Al-Ali
9,119,595 B2 9/2015 Lamego
9,131,881 B2 9/2015 Diab et al.
9,131,882 B2 9/2015 Al-Ali et al.
9,131,883 B2 9/2015 Al-Ali
9,131,917 B2 9/2015 Telfort et al.
9,138,180 B1 9/2015 Coverston et al.
9,138,182 B2 9/2015 Al-Ali et al.
9,138,192 B2 9/2015 Weber et al.
9,142,117 B2 9/2015 Muhsin et al.
9,153,112 B1 10/2015 Kiani et al.
9,153,121 B2 10/2015 Kiani et al.
9,161,696 B2 10/2015 Al-Ali et al.
9,161,713 B2 10/2015 Al-Ali et al.
9,167,995 B2 10/2015 Lamego et al.
9,176,141 B2 11/2015 Al-Ali et al.
9,186,102 B2 11/2015 Bruinsma et al.
9,192,312 B2 11/2015 Al-Ali
9,192,329 B2 11/2015 Ai-Ali
9,192,351 B1 11/2015 Telfort et al.
9,195,385 B2 11/2015 Al-Ali et al.
9,211,072 B2 12/2015 Kiani
9,211,095 B1 12/2015 Al-Ali
9,218,454 B2 12/2015 Kiani et al.
9,226,696 B2 1/2016 Kiani
9,241,662 B2 1/2016 Al-Ali et al.
9,245,668 B1 1/2016 Vo et al.
9,259,185 B2 2/2016 Abdul-Hafiz et al.
9,267,572 B2 2/2016 Barker et al.
9,277,880 B2 3/2016 Poeze et al.
9,289,167 B2 3/2016 Diab et al.
9,295,421 B2 3/2016 Kiani et al.
9,307,928 B1 4/2016 Al-Ali et al.
9,323,894 B2 4/2016 Kiani
D755,392 S 5/2016 Hwang et al.
9,326,712 B1 5/2016 Kiani
9,333,316 B2 5/2016 Kiani
9,339,220 B2 5/2016 Lamego et al.
9,341,565 B2 5/2016 Lamego et al.
9,351,673 B2 5/2016 Diab et al.
9,351,675 B2 5/2016 Al-Ali et al.
9,364,181 B2 6/2016 Kiani et al.
9,368,671 B2 6/2016 Wojtczuk et al.
9,370,325 B2 6/2016 Al-Ali et al.
9,370,326 B2 6/2016 McHale et al.
9,370,335 B2 6/2016 Al-Ali et al.
9,375,185 B2 6/2016 Ali et al.
9,386,953 B2 7/2016 Al-Ali
9,386,961 B2 7/2016 Al-Ali et al.
9,392,945 B2 7/2016 Al-Ali et al.
9,397,448 B2 7/2016 Al-Ali et al.
9,408,542 B1 8/2016 Kinast et al.
9,436,645 B2 9/2016 Al-Ali et al.
9,445,759 B1 9/2016 Lamego et al.
9,466,919 B2 10/2016 Kiani et al.
9,474,474 B2 10/2016 Lamego et al.
9,480,422 B2 11/2016 Al-Ali
9,480,435 B2 11/2016 Olsen
9,492,110 B2 11/2016 Al-Ali et al.
9,510,779 B2 12/2016 Poeze et al.
9,517,024 B2 12/2016 Kiani et al.
9,532,722 B2 1/2017 Lamego et al.
9,538,949 B2 1/2017 Al-Ali et al.
9,538,980 B2 1/2017 Telfort et al.
9,549,696 B2 1/2017 Lamego et al.
9,554,737 B2 1/2017 Schurman et al.
9,560,996 B2 2/2017 Kiani
9,560,998 B2 2/2017 Al-Ali et al.
9,566,019 B2 2/2017 Al-Ali et al.
9,579,039 B2 2/2017 Jansen et al.
9,591,975 B2 3/2017 Dalvi et al.
9,622,692 B2 4/2017 Lamego et al.
9,622,693 B2 4/2017 Diab
D788,312 S 5/2017 Al-Ali et al.
9,636,055 B2 5/2017 Al Ali et al.
9,636,056 B2 5/2017 Al-Ali
9,649,054 B2 5/2017 Lamego et al.
9,662,052 B2 5/2017 Al-Ali et al.
9,668,679 B2 6/2017 Schurman et al.
9,668,680 B2 6/2017 Bruinsma et al.
9,668,703 B2 6/2017 Al-Ali
9,675,286 B2 6/2017 Diab
9,687,160 B2 6/2017 Kiani
9,693,719 B2 7/2017 Al-Ali et al.
9,693,737 B2 7/2017 Al-Ali
9,697,928 B2 7/2017 Al-Ali et al.
9,717,425 B2 8/2017 Kiani et al.
9,717,458 B2 8/2017 Lamego et al.
9,724,016 B1 8/2017 Al-Ali et al.
9,724,024 B2 8/2017 Ai-Ali
9,724,025 B1 8/2017 Kiani et al.
9,730,640 B2 8/2017 Diab et al.
9,743,887 B2 8/2017 Al-Ali et al.
9,749,232 B2 8/2017 Sampath et al.
9,750,442 B2 9/2017 Olsen
9,750,443 B2 9/2017 Smith et al.
9,750,461 B1 9/2017 Telfort
9,775,545 B2 10/2017 Al-Ali et al.
9,775,546 B2 10/2017 Diab et al.
9,775,570 B2 10/2017 Al-Ali
9,778,079 B1 10/2017 Al-Ali et al.
9,782,077 B2 10/2017 Lamego et al.
9,782,110 B2 10/2017 Kiani

(56) References Cited

U.S. PATENT DOCUMENTS 9,787,568 B2 10/2017 Lamego et al.
9,788,735 B2 10/2017 Al-Ali
9,788,768 B2 10/2017 Al-Ali et al.
9,795,300 B2 10/2017 Al-Ali
9,795,310 B2 10/2017 Al-Ali
9,795,358 B2 10/2017 Telfort et al.
9,795,739 B2 10/2017 Al-Ali et al.
9,801,556 B2 10/2017 Kiani
9,801,588 B2 10/2017 Weber et al.
9,808,188 B1 11/2017 Perea et al.
9,814,418 B2 11/2017 Weber et al.
9,820,691 B2 11/2017 Kiani
9,833,152 B2 12/2017 Kiani et al.
9,833,180 B2 12/2017 Shakespeare et al.
9,839,379 B2 12/2017 Al-Ali et al.
9,839,381 B1 12/2017 Weber et al.
9,847,002 B2 12/2017 Kiani et al.
9,847,749 B2 12/2017 Kiani et al.
9,848,800 B1 12/2017 Lee et al.
9,848,806 B2 12/2017 Al-Ali
9,848,807 B2 12/2017 Lamego
9,861,298 B2 1/2018 Eckerbom et al.
9,861,304 B2 1/2018 Al-Ali et al.
9,861,305 B1 1/2018 Weber et al.
9,867,578 B2 1/2018 Al-Ali et al.
9,872,623 B2 1/2018 Al-Ali
9,876,320 B2 1/2018 Coverston et al.
9,877,650 B2 1/2018 Muhsin et al.
9,877,686 B2 1/2018 Al-Ali et al.
9,891,079 B2 2/2018 Dalvi
9,895,107 B2 2/2018 Al-Ali et al.
9,913,617 B2 3/2018 Al-Ali et al.
9,924,893 B2 3/2018 Schurman et al.
9,924,897 B1 3/2018 Abdul-Hafiz
9,936,917 B2 4/2018 Poeze et al.
9,943,269 B2 4/2018 Muhsin et al.
9,949,676 B2 4/2018 Al-Ali
9,955,937 B2 5/2018 Telfort
9,965,946 B2 5/2018 Al-Ali et al.
9,980,667 B2 5/2018 Kiani et al.
D820,865 S 6/2018 Muhsin et al.
9,986,919 B2 6/2018 Lamego et al.
9,986,952 B2 6/2018 Dalvi et al.
9,989,560 B2 6/2018 Poeze et al.
9,993,207 B2 6/2018 Al-Ali et al.
10,007,758 B2 6/2018 Al-Ali et al.
D822,215 S 7/2018 Al-Ali et al.
D822,216 S 7/2018 Barker et al.
10,010,276 B2 7/2018 Al-Ali et al.
10,032,002 B2 7/2018 Kiani et al.
10,039,482 B2 8/2018 Al-Ali et al.
10,052,037 B2 8/2018 Kinast et al.
10,058,275 B2 8/2018 Al-Ali et al.
10,064,562 B2 9/2018 Ai-Ali
10,086,138 B1 10/2018 Novak, Jr.
10,092,200 B2 10/2018 Al-Ali et al.
10,092,249 B2 10/2018 Kiani et al.
10,098,550 B2 10/2018 Al-Ali et al.
10,098,591 B2 10/2018 Al-Ali et al.
10,098,610 B2 10/2018 Al-Ali et al.
10,111,591 B2 10/2018 Dyell et al.
D833,624 S 11/2018 DeJong et al.
10,123,726 B2 11/2018 Al-Ali et al.
10,123,729 B2 11/2018 Dyell et al.
10,130,289 B2 11/2018 Al-Ali et al.
10,130,291 B2 11/2018 Schurman et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,296 B2 1/2019 Al-Ali et al.
10,188,331 B1 1/2019 Kiani et al.
10,188,348 B2 1/2019 Al-Ali et al.
RE47,218 E 2/2019 Ai-Ali
RE47,244 E 2/2019 Kiani et al.
RE47,249 E 2/2019 Kiani et al.
10,194,847 B2 2/2019 Al-Ali
10,194,848 B1 2/2019 Kiani et al.
10,201,298 B2 2/2019 Al-Ali et al.
10,205,272 B2 2/2019 Kiani et al.
10,205,291 B2 2/2019 Scruggs et al.
10,213,108 B2 2/2019 Al-Ali
10,219,706 B2 3/2019 Al-Ali
10,219,746 B2 3/2019 McHale et al.
10,226,187 B2 3/2019 Al-Ali et al.
10,226,576 B2 3/2019 Kiani
10,231,657 B2 3/2019 Al-Ali et al.
10,231,670 B2 3/2019 Blank et al.
10,231,676 B2 3/2019 Al-Ali et al.
RE47,353 E 4/2019 Kiani et al.
10,251,585 B2 4/2019 Al-Ali et al.
10,251,586 B2 4/2019 Lamego
10,255,994 B2 4/2019 Sampath et al.
10,258,265 B1 4/2019 Poeze et al.
10,258,266 B1 4/2019 Poeze et al.
10,271,748 B2 4/2019 Al-Ali
10,278,626 B2 5/2019 Schurman et al.
10,278,648 B2 5/2019 Al-Ali et al.
10,279,247 B2 5/2019 Kiani
10,292,628 B1 5/2019 Poeze et al.
10,292,657 B2 5/2019 Abdul-Hafiz et al.
10,292,664 B2 5/2019 Al-Ali
10,299,708 B1 5/2019 Poeze et al.
10,299,709 B2 5/2019 Perea et al.
10,299,720 B2 5/2019 Brown et al.
10,305,775 B2 5/2019 Lamego et al.
10,307,111 B2 6/2019 Muhsin et al.
10,325,681 B2 6/2019 Sampath et al.
10,327,337 B2 6/2019 Schmidt et al.
10,327,713 B2 6/2019 Barker et al.
10,332,630 B2 6/2019 Ai-Ali
10,335,033 B2 7/2019 Ai-Ali
10,335,068 B2 7/2019 Poeze et al.
10,335,072 B2 7/2019 Al-Ali et al.
10,342,470 B2 7/2019 Al-Ali et al.
10,342,487 B2 7/2019 Al-Ali et al.
10,342,497 B2 7/2019 Al-Ali et al.
10,349,895 B2 7/2019 Telfort et al.
10,349,898 B2 7/2019 Al-Ali et al.
10,354,504 B2 7/2019 Kiani et al.
10,357,206 B2 7/2019 Weber et al.
10,357,209 B2 7/2019 Ai-Ai
10,366,787 B2 7/2019 Sampath et al.
10,368,787 B2 8/2019 Reichgott et al.
10,376,190 B1 8/2019 Poeze et al.
10,376,191 B1 8/2019 Poeze et al.
10,383,520 B2 8/2019 Wojtczuk et al.
10,383,527 B2 8/2019 Al-Ali
10,388,120 B2 8/2019 Muhsin et al.
10,398,320 B2 9/2019 Kiani et al.
10,405,804 B2 9/2019 Al-Ali
10,413,666 B2 9/2019 Al-Ali et al.
10,420,493 B2 9/2019 Al-Ali et al.
D864,120 S 10/2019 Forrest et al.
10,433,776 B2 10/2019 Al-Ali
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,284 B2 11/2019 Al-Ali et al.
10,463,340 B2 11/2019 Telfort et al.
10,470,695 B2 11/2019 Al-Ali et al.
10,471,159 B1 11/2019 Lapotko et al.
10,478,107 B2 11/2019 Kiani et al.
10,503,379 B2 12/2019 Al-Ali et al.
10,505,311 B2 12/2019 Al-Ali et al.
10,512,436 B2 12/2019 Muhsin et al.
10,524,706 B2 1/2020 Telfort et al.
10,524,738 B2 1/2020 Olsen
10,531,811 B2 1/2020 Al-Ali et al.

(56) References Cited

U.S. PATENT DOCUMENTS

| | | | |
|---|---|---|---|
| 10,531,819 | B2 | 1/2020 | Diab et al. |
| 10,531,835 | B2 | 1/2020 | Al-Ali et al. |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| RE47,882 | E | 3/2020 | Al-Ali |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Ai-Ai |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali et al. |
| D1,037,462 | S | 7/2024 | Al-Ali et al. |
| 12,029,844 | B2 | 7/2024 | Pauley et al. |
| 12,042,285 | B1 | 7/2024 | Iyengar et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |

(56) References Cited

U.S. PATENT DOCUMENTS 12,198,790 B1 1/2025 Ai-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin et al.
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
12,495,967 B2 12/2025 Muhsin et al.
2001/0034477 A1 10/2001 Mansfield et al.
2001/0039483 A1 11/2001 Brand et al.
2002/0010401 A1 1/2002 Bushmakin et al.
2002/0026106 A1* 2/2002 Khalil ................ G01N 21/4795 600/310
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0088164 A1* 5/2003 Stetson ............. A61B 5/14551 600/323
2003/0144582 A1 7/2003 Cohen et al.
2003/0156288 A1 8/2003 Barnum et al.
2003/0212312 A1 11/2003 Coffin, IV et al.
2004/0039271 A1 2/2004 Blank et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0088226 A1 4/2007 Spence et al.
2007/0179369 A1 8/2007 Baker, Jr.
2007/0180140 A1 8/2007 Welch et al.
2007/0244377 A1 10/2007 Cozad et al.
2007/0282478 A1 12/2007 Al-Ali et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275813 A1 11/2009 Davis
2009/0275844 A1 11/2009 Al-Ali
2009/0299157 A1 12/2009 Telfort et al.
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2011/0001605 A1 1/2011 Kiani et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0105854 A1 5/2011 Kiani et al.
2011/0118561 A1 5/2011 Tari et al.
2011/0124769 A1 5/2011 Moen et al.
2011/0137297 A1 6/2011 Kiani et al.
2011/0172498 A1 7/2011 Olsen et al.
2011/0196211 A1* 8/2011 Al-Ali ...................... A61B 7/04 600/300
2011/0208015 A1 8/2011 Welch et al.
2011/0209915 A1 9/2011 Telfort et al.
2011/0213212 A1 9/2011 Al-Ali
2011/0230733 A1 9/2011 Al-Ali
2011/0237911 A1 9/2011 Lamego et al.
2012/0059267 A1 3/2012 Lamego et al.
2012/0123231 A1 5/2012 O'Reilly
2012/0165629 A1 6/2012 Merritt et al.
2012/0179006 A1 7/2012 Jansen et al.
2012/0209082 A1 8/2012 Al-Ali
2012/0209084 A1 8/2012 Olsen et al.
2012/0226117 A1 9/2012 Lamego et al.
2012/0227739 A1 9/2012 Kiani
2012/0283524 A1 11/2012 Kiani et al.
2012/0296178 A1 11/2012 Lamego et al.
2012/0319816 A1 12/2012 Al-Ali
2012/0330112 A1 12/2012 Lamego et al.
2013/0023775 A1 1/2013 Lamego et al.
2013/0041591 A1 2/2013 Lamego
2013/0045685 A1 2/2013 Kiani
2013/0046204 A1 2/2013 Lamego et al.
2013/0060147 A1 3/2013 Welch et al.
2013/0096405 A1 4/2013 Garfio
2013/0096936 A1 4/2013 Sampath et al.
2013/0190581 A1 7/2013 Al-Ali et al.
2013/0197328 A1 8/2013 Diab et al.
2013/0211214 A1 8/2013 Olsen
2013/0243021 A1 9/2013 Siskavich
2013/0253334 A1 9/2013 Al-Ali et al.
2013/0296672 A1 11/2013 O'Neil et al.
2013/0296713 A1 11/2013 Al-Ali et al.
2013/0317370 A1 11/2013 Dalvi et al.
2013/0324808 A1 12/2013 Al-Ali et al.
2013/0331670 A1 12/2013 Kiani
2013/0338461 A1 12/2013 Lamego et al.
2013/0345921 A1 12/2013 Al-Ali et al.
2014/0012100 A1 1/2014 Al-Ali et al.
2014/0034353 A1 2/2014 Al-Ali et al.
2014/0051953 A1 2/2014 Lamego et al.
2014/0058230 A1 2/2014 Abdul-Hafiz et al.
2014/0058232 A1* 2/2014 Andrijauskas ....... A61B 5/1495 600/328
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0094667 A1 4/2014 Schurman et al.
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0121483 A1 5/2014 Kiani
2014/0127137 A1 5/2014 Bellott et al.
2014/0129702 A1 5/2014 Lamego et al.
2014/0135588 A1 5/2014 Al-Ali et al.
2014/0142401 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187973 A1 7/2014 Brown et al.
2014/0194709 A1 7/2014 Al-Ali et al.

(56) References Cited

U.S. PATENT DOCUMENTS

2014/0194711 A1 7/2014 Ai-Ali
2014/0194766 A1 7/2014 Al-Ali et al.
2014/0206963 A1 7/2014 Al-Ali
2014/0213864 A1 7/2014 Abdul-Hafiz et al.
2014/0243627 A1 8/2014 Diab et al.
2014/0266790 A1 9/2014 Al-Ali et al.
2014/0275808 A1 9/2014 Poeze et al.
2014/0275835 A1 9/2014 Lamego et al.
2014/0275871 A1 9/2014 Lamego et al.
2014/0275872 A1 9/2014 Merritt et al.
2014/0275881 A1 9/2014 Lamego et al.
2014/0288400 A1 9/2014 Diab et al.
2014/0303520 A1 10/2014 Telfort et al.
2014/0316217 A1 10/2014 Purdon et al.
2014/0316218 A1 10/2014 Purdon et al.
2014/0316228 A1 10/2014 Blank et al.
2014/0323825 A1 10/2014 Al-Ali et al.
2014/0323897 A1 10/2014 Brown et al.
2014/0323898 A1 10/2014 Purdon et al.
2014/0330092 A1 11/2014 Al-Ali et al.
2014/0330098 A1 11/2014 Merritt et al.
2014/0330099 A1 11/2014 Al-Ali et al.
2014/0333440 A1 11/2014 Kiani
2014/0336481 A1 11/2014 Shakespeare et al.
2014/0343436 A1 11/2014 Kiani
2014/0357966 A1 12/2014 Al-Ali et al.
2015/0005600 A1 1/2015 Blank et al.
2015/0011907 A1 1/2015 Purdon et al.
2015/0018650 A1 1/2015 Al-Ali et al.
2015/0032029 A1 1/2015 Al-Ali et al.
2015/0038859 A1 2/2015 Dalvi et al.
2015/0073241 A1 3/2015 Lamego
2015/0080754 A1 3/2015 Purdon et al.
2015/0087936 A1 3/2015 Al-Ali et al.
2015/0094546 A1 4/2015 Al-Ali
2015/0099950 A1 4/2015 Al-Ali et al.
2015/0101844 A1 4/2015 Al-Ali et al.
2015/0106121 A1 4/2015 Muhsin et al.
2015/0112151 A1 4/2015 Muhsin et al.
2015/0165312 A1 6/2015 Kiani
2015/0196249 A1 7/2015 Brown et al.
2015/0216459 A1 8/2015 Al-Ali et al.
2015/0238722 A1 8/2015 Al-Ali
2015/0245773 A1 9/2015 Lamego et al.
2015/0245794 A1 9/2015 Al-Ali
2015/0257689 A1 9/2015 Al-Ali et al.
2015/0272514 A1 10/2015 Kiani et al.
2015/0351697 A1 12/2015 Weber et al.
2015/0359429 A1 12/2015 Al-Ali et al.
2015/0366507 A1 12/2015 Blank et al.
2016/0029932 A1 2/2016 Al-Ali
2016/0058347 A1 3/2016 Reichgott et al.
2016/0066824 A1 3/2016 Al-Ali et al.
2016/0081552 A1 3/2016 Wojtczuk et al.
2016/0095543 A1 4/2016 Telfort et al.
2016/0095548 A1 4/2016 Al-Ali et al.
2016/0103598 A1 4/2016 Al-Ali et al.
2016/0166182 A1 6/2016 Al-Ali et al.
2016/0166183 A1 6/2016 Poeze et al.
2016/0196388 A1 7/2016 Lamego
2016/0197436 A1 7/2016 Barker et al.
2016/0213281 A1 7/2016 Eckerbom et al.
2016/0228043 A1 8/2016 O'Neil et al.
2016/0233632 A1 8/2016 Scruggs et al.
2016/0234944 A1 8/2016 Schmidt et al.
2016/0270735 A1 9/2016 Diab et al.
2016/0283665 A1 9/2016 Sampath et al.
2016/0287090 A1 10/2016 Al-Ali et al.
2016/0287786 A1 10/2016 Kiani
2016/0296169 A1 10/2016 McHale et al.
2016/0310052 A1 10/2016 Al-Ali et al.
2016/0314260 A1 10/2016 Kiani
2016/0324488 A1 11/2016 Olsen
2016/0327984 A1 11/2016 Al-Ali et al.
2016/0331332 A1 11/2016 Al-Ali
2016/0367173 A1 12/2016 Dalvi et al.
2017/0000394 A1 1/2017 Al-Ali et al.
2017/0007134 A1 1/2017 Al-Ali et al.
2017/0007198 A1 1/2017 Al-Ali et al.
2017/0014083 A1 1/2017 Diab et al.
2017/0014084 A1 1/2017 Al-Ali et al.
2017/0024748 A1 1/2017 Haider
2017/0042488 A1 2/2017 Muhsin
2017/0055851 A1 3/2017 Ai-Ai
2017/0055882 A1 3/2017 Al-Ali et al.
2017/0055887 A1 3/2017 Al-Ali
2017/0055896 A1 3/2017 Al-Ali
2017/0079594 A1 3/2017 Telfort et al.
2017/0086723 A1 3/2017 Al-Ali et al.
2017/0143281 A1 5/2017 Olsen
2017/0147774 A1 5/2017 Kiani
2017/0156620 A1 6/2017 Al-Ali et al.
2017/0173632 A1 6/2017 Al-Ali
2017/0187146 A1 6/2017 Kiani et al.
2017/0188919 A1 7/2017 Al-Ali et al.
2017/0196464 A1 7/2017 Jansen et al.
2017/0196470 A1 7/2017 Lamego et al.
2017/0224262 A1 8/2017 Al-Ali
2017/0228516 A1 8/2017 Sampath et al.
2017/0245790 A1 8/2017 Al-Ali et al.
2017/0251974 A1 9/2017 Shreim et al.
2017/0251975 A1 9/2017 Shreim et al.
2017/0258403 A1 9/2017 Abdul-Hafiz et al.
2017/0311851 A1 11/2017 Schurman et al.
2017/0311891 A1 11/2017 Kiani et al.
2017/0325728 A1 11/2017 Al-Ali et al.
2017/0332976 A1 11/2017 Al-Ali
2017/0340293 A1 11/2017 Al-Ali et al.
2017/0360310 A1 12/2017 Kiani
2017/0367632 A1 12/2017 Al-Ali et al.
2018/0008146 A1 1/2018 Al-Ali et al.
2018/0013562 A1 1/2018 Haider et al.
2018/0014752 A1 1/2018 Al-Ali et al.
2018/0028124 A1 2/2018 Al-Ali et al.
2018/0055385 A1 3/2018 Al-Ali
2018/0055390 A1 3/2018 Kiani et al.
2018/0055430 A1 3/2018 Diab et al.
2018/0064381 A1 3/2018 Shakespeare et al.
2018/0069776 A1 3/2018 Lamego et al.
2018/0070867 A1 3/2018 Smith et al.
2018/0082767 A1 3/2018 Al-Ali et al.
2018/0085068 A1 3/2018 Telfort
2018/0087937 A1 3/2018 Al-Ali et al.
2018/0103874 A1 4/2018 Lee et al.
2018/0103905 A1 4/2018 Kiani
2018/0110478 A1 4/2018 Al-Ali
2018/0116575 A1 5/2018 Perea et al.
2018/0125368 A1 5/2018 Lamego et al.
2018/0125430 A1 5/2018 Al-Ali et al.
2018/0125445 A1 5/2018 Telfort et al.
2018/0130325 A1 5/2018 Kiani et al.
2018/0132769 A1 5/2018 Weber et al.
2018/0132770 A1 5/2018 Lamego
2018/0146901 A1 5/2018 Al-Ali et al.
2018/0146902 A1 5/2018 Kiani et al.
2018/0153442 A1 6/2018 Eckerbom et al.
2018/0153446 A1 6/2018 Kiani
2018/0153447 A1 6/2018 Al-Ali et al.
2018/0153448 A1 6/2018 Weber et al.
2018/0161499 A1 6/2018 Al-Ali et al.
2018/0168491 A1 6/2018 Al-Ali et al.
2018/0174679 A1 6/2018 Sampath et al.
2018/0174680 A1 6/2018 Sampath et al.
2018/0182484 A1 6/2018 Sampath et al.
2018/0184917 A1 7/2018 Kiani
2018/0192924 A1 7/2018 Al-Ali
2018/0192953 A1 7/2018 Shreim et al.
2018/0192955 A1 7/2018 Al-Ali et al.
2018/0199871 A1 7/2018 Pauley et al.
2018/0206795 A1 7/2018 Al-Ali
2018/0206815 A1 7/2018 Telfort
2018/0213583 A1 7/2018 Al-Ali
2018/0214031 A1 8/2018 Kiani et al.
2018/0214090 A1 8/2018 Al-Ali et al.

(56) References Cited

U.S. PATENT DOCUMENTS

2018/0218792 A1 8/2018 Muhsin et al.
2018/0225960 A1 8/2018 Al-Ali et al.
2018/0238718 A1 8/2018 Dalvi
2018/0242853 A1 8/2018 Al-Ali
2018/0242921 A1 8/2018 Muhsin et al.
2018/0242923 A1 8/2018 Al-Ali et al.
2018/0242924 A1 8/2018 Barker et al.
2018/0242926 A1 8/2018 Muhsin et al.
2018/0247353 A1 8/2018 Al-Ali et al.
2018/0247712 A1 8/2018 Muhsin et al.
2018/0249933 A1 9/2018 Schurman et al.
2018/0253947 A1 9/2018 Muhsin et al.
2018/0256087 A1 9/2018 Al-Ali et al.
2018/0256113 A1 9/2018 Weber et al.
2018/0285094 A1 10/2018 Housel et al.
2018/0289325 A1 10/2018 Poeze et al.
2018/0289337 A1 10/2018 Al-Ali et al.
2018/0296161 A1 10/2018 Shreim et al.
2018/0300919 A1 10/2018 Muhsin et al.
2018/0310822 A1 11/2018 Indorf et al.
2018/0310823 A1 11/2018 Al-Ali et al.
2018/0317826 A1 11/2018 Muhsin et al.
2018/0317841 A1 11/2018 Novak, Jr.
2018/0333055 A1 11/2018 Lamego et al.
2018/0333087 A1 11/2018 Al-Ali
2019/0000317 A1 1/2019 Muhsin et al.
2019/0000362 A1 1/2019 Kiani et al.
2019/0015023 A1 1/2019 Monfre
2019/0021638 A1 1/2019 Al-Ali et al.
2019/0029574 A1 1/2019 Schurman et al.
2019/0029578 A1 1/2019 Al-Ali et al.
2019/0038143 A1 2/2019 Al-Ali
2019/0058280 A1 2/2019 Al-Ali et al.
2019/0058281 A1 2/2019 Al-Ali et al.
2019/0069813 A1 3/2019 Al-Ali
2019/0069814 A1 3/2019 Ai-Ali
2019/0076028 A1 3/2019 Al-Ali et al.
2019/0082979 A1 3/2019 Al-Ali et al.
2019/0090748 A1 3/2019 Al-Ali
2019/0090760 A1 3/2019 Kinast et al.
2019/0090764 A1 3/2019 Al-Ali
2019/0104973 A1 4/2019 Poeze et al.
2019/0110719 A1 4/2019 Poeze et al.
2019/0117070 A1 4/2019 Muhsin et al.
2019/0117139 A1 4/2019 Al-Ali et al.
2019/0117140 A1 4/2019 Al-Ali et al.
2019/0117141 A1 4/2019 Al-Ali
2019/0117930 A1 4/2019 Ai-Ali
2019/0122763 A1 4/2019 Sampath et al.
2019/0133525 A1 5/2019 Al-Ali et al.
2019/0142283 A1 5/2019 Lamego et al.
2019/0142344 A1 5/2019 Telfort et al.
2019/0150800 A1 5/2019 Poeze et al.
2019/0150856 A1 5/2019 Kiani et al.
2019/0167161 A1 6/2019 Al-Ali et al.
2019/0175019 A1 6/2019 Al-Ali et al.
2019/0192076 A1 6/2019 McHale et al.
2019/0200941 A1 7/2019 Chandran et al.
2019/0201623 A1 7/2019 Kiani
2019/0209025 A1 7/2019 Al-Ali
2019/0214778 A1 7/2019 Scruggs et al.
2019/0216319 A1 7/2019 Poeze et al.
2019/0216379 A1 7/2019 Al-Ali et al.
2019/0221966 A1 7/2019 Kiani et al.
2019/0223804 A1 7/2019 Blank et al.
2019/0231199 A1 8/2019 Al-Ali et al.
2019/0231241 A1 8/2019 Al-Ali et al.
2019/0231270 A1 8/2019 Abdul-Hafiz et al.
2019/0239787 A1 8/2019 Pauley et al.
2019/0239824 A1 8/2019 Muhsin et al.
2019/0254578 A1 8/2019 Lamego
2019/0261857 A1 8/2019 Al-Ali
2019/0269370 A1 9/2019 Al-Ali et al.
2019/0274606 A1 9/2019 Kiani et al.
2019/0274627 A1 9/2019 Al-Ali et al.
2019/0274635 A1 9/2019 Al-Ali et al.
2019/0290136 A1 9/2019 Dalvi et al.
2019/0298270 A1 10/2019 Al-Ali et al.
2019/0304601 A1 10/2019 Sampath et al.
2019/0304605 A1 10/2019 Al-Ali
2019/0307377 A1 10/2019 Perea et al.
2019/0320906 A1 10/2019 Olsen
2019/0320959 A1 10/2019 Al-Ali
2019/0320988 A1 10/2019 Ahmed et al.
2019/0325722 A1 10/2019 Kiani et al.
2019/0350506 A1 11/2019 Al-Ali et al.
2019/0357812 A1 11/2019 Poeze et al.
2019/0357813 A1 11/2019 Poeze et al.
2019/0357823 A1 11/2019 Reichgott et al.
2019/0357824 A1 11/2019 Al-Ali et al.
2019/0358524 A1 11/2019 Kiani
2019/0365294 A1 12/2019 Poeze et al.
2019/0365295 A1 12/2019 Poeze et al.
2019/0374135 A1 12/2019 Poeze et al.
2019/0374139 A1 12/2019 Kiani et al.
2019/0374173 A1 12/2019 Kiani et al.
2019/0374713 A1 12/2019 Kiani et al.
2019/0386908 A1 12/2019 Lamego et al.
2019/0388039 A1 12/2019 Al-Ali
2020/0000338 A1 1/2020 Lamego et al.
2020/0000340 A1 1/2020 Wojtczuk et al.
2020/0000415 A1 1/2020 Barker et al.
2020/0015716 A1 1/2020 Poeze et al.
2020/0021930 A1 1/2020 Iswanto et al.
2020/0029867 A1 1/2020 Poeze et al.
2020/0037453 A1 1/2020 Triman et al.
2020/0037891 A1 2/2020 Kiani et al.
2020/0037966 A1 2/2020 Al-Ali
2020/0060869 A1 2/2020 Telfort et al.
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138288 A1 5/2020 Al-Ali et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.

(56) References Cited

U.S. PATENT DOCUMENTS

2022/0151521 A1 5/2022 Krishnamani et al.
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Ai-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.

* cited by examiner

PHYSIOLOGICAL MEASUREMENT CALIBRATION

PRIORITY CLAIM

The present application is a continuation of U.S. patent application Ser. No. 17/061,945, filed Oct. 2, 2020, titled "Physiological Measurement Calibration", which is a continuation of U.S. patent application Ser. No. "15/499,806, filed Apr. 27, 2017, titled "Physiological Measurement Calibration", now U.S. Pat. No. 10,827,961, issued Nov. 10, 2020, which is a continuation of U.S. patent application Ser. No. 14/160,322, filed Jan. 21, 2014, titled "Physiological Measurement Calibration", which is a continuation-in-part of U.S. patent application Ser. No. 14/011,567, filed Aug. 27, 2013, titled "Physiological Measurement Calibration", which claims priority benefit under 35 U.S.C. § 119(c) to U.S. Provisional Patent Application Ser. No. 61/694,723, filed Aug. 29, 2012, titled Physiological Measurement Calibration, and U.S. Provisional Patent Application Ser. No. 61/713,833, filed Oct. 15, 2012, titled Physiological Measurement Calibration, each of which is hereby incorporated in its entirety by reference herein.

RELATED APPLICATIONS

The present Application is related to the following patents and patent applications: U.S. Pat. No. 6,606,511, titled "PULSE OXIMETRY PULSE INDICATOR," filed on Jan. 6, 2000, and issued on Aug. 12, 2003; U.S. Pat. No. 7,764,982, titled "MULTIPLE WAVELENGTH SENSOR EMITTERS," filed on Mar. 1, 2006, and issued on Jul. 27, 2010; U.S. Pat. No. 8,130,105, titled "NON-INVASIVE MULTI-PARAMETER PATIENT MONITOR," filed on Mar. 1, 2006, and issued on Mar. 6, 2012; U.S. patent application Ser. No. 12/011,011, entitled "PERFUSION TREND INDICATOR," filed on Jan. 22, 2008, and published as U.S. Patent Application Publication No. 2008/0221464 on Sep. 11, 2008; U.S. patent application Ser. No. 12/783,436, entitled "HEMOGLOBIN DISPLAY AND PATIENT TREATMENT," filed on May 19, 2010, and published as U.S. Patent Application No. 2010/0298675 on Nov. 25, 2010.

The U.S. Patents and Patent Application Publications referenced above are expressly bodily incorporated in their entirety, and are part of the present disclosure. All embodiments described herein are compatible with and/or are components of the embodiments described in the above reference patents and patent applications. Some or all of the features described herein can be used or otherwise combined with any of the features described in the Appendices.

BACKGROUND

Multiple wavelength optical sensors can be used to non-invasively measure physiological parameters, such as $SpO_2$, HbCO, HbMet, perfusion index (PI), non-invasive total hemoglobin (SpHb), and other physiological parameters. Noninvasive physiological measurements are often affected by a number of different variables. These variables can include differences in manufacturing tolerances between devices, differences in skin pigmentation and bone structure among patients, operating temperatures, movement, as well as a host of other variables that are often difficult to determine and account for, including, for example, various changes in a patient's physiology that may occur during a measurement.

In some current approaches, a multiple wavelength optical sensor causes light of several wavelengths to be shined into the measurement site of a patient's tissue. The tissue of the patient attenuates the light, which is then detected by a detector. The detected signal is sent to a processor for processing. One drawback of these current measurement systems, among others, is that determining a physiological measurement based on the raw detected signal can be difficult, and often requires a number of different considerations pertaining to other physiological parameters.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

The present disclosure provides a robust calibration technique for physiological measurements of interest. In particular, the present disclosure provides a mapping to calibrate observed measurements so that they are less affected, or entirely unaffected, by variables that can affect the observed measurements of the parameters. For example, in one embodiment, robust non-invasive total hemoglobin (SpHb) measurements are made such that changes in a patient's perfusion (as can be measured by a perfusion index (PI)), do not affect the observed measurements of SpHb.

BRIEF DESCRIPTION OF THE DRAWINGS

The foregoing aspects and many of the attendant advantages will become more readily appreciated as the same become better understood by reference to the following detailed description when taken in conjunction with the accompanying drawings, wherein.

DETAILED DESCRIPTION

Overview of the Present Disclosure

Figure 1:
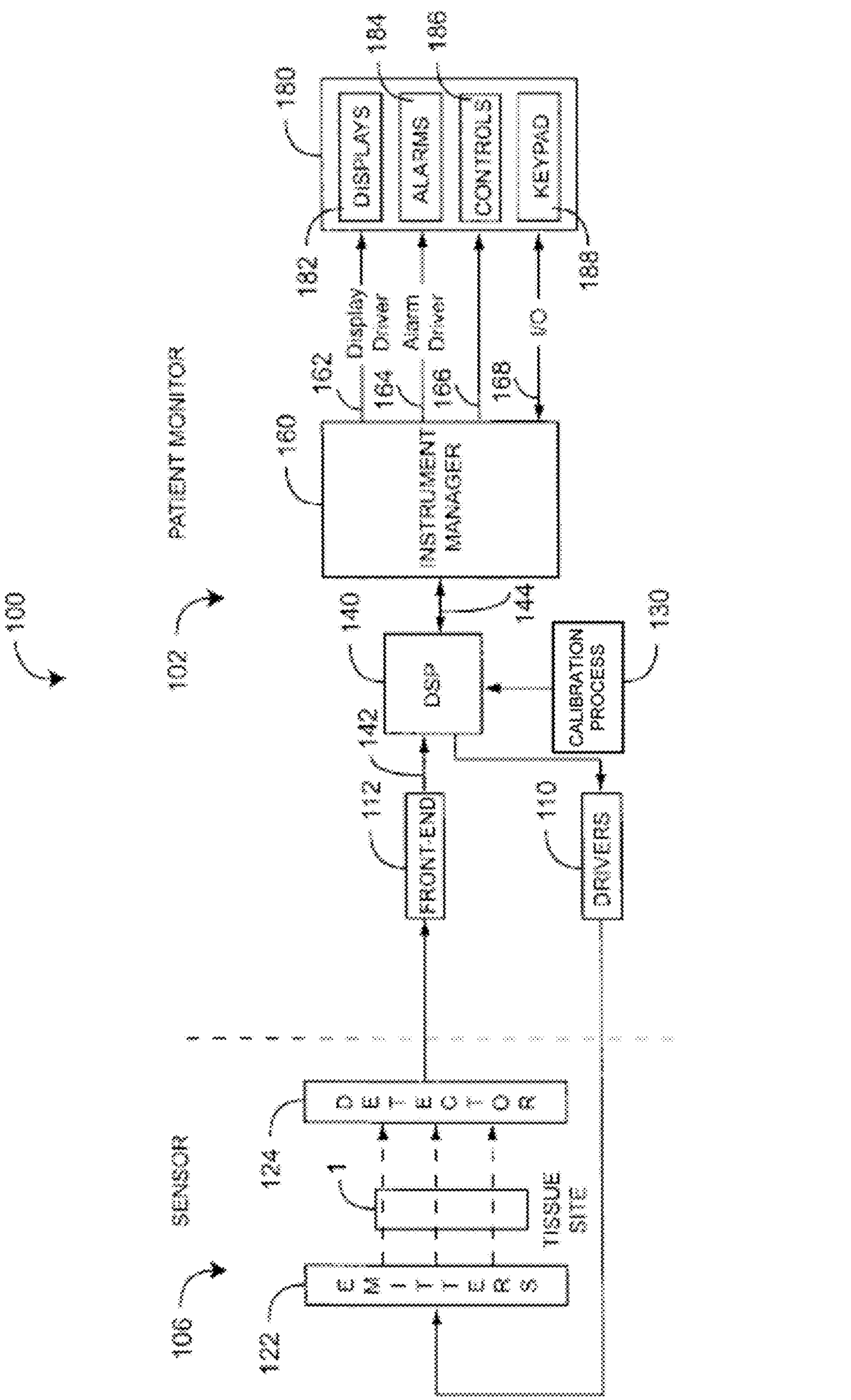
FIG. 1 is a general block diagram of a physiological measurement system that can be calibrated according to techniques of the present disclosure.

The observation of some physiological measurements can be affected by changes in other physiological parameters. For example, an observed SpHb measurement can be affected by how perfused a patient is. Other variables can also affect an SpHb measurement such as, for example, temperature, desaturation, and other physiological parameters. Of course, it is to be understood that the present disclosure is not limited to the correction of SpHb, but more generally relates to measurement calibration of any physiological parameter that can be affected by a related parameter.

Typically, a vast amount of testing is performed on many different patients in order to determine an calibration equation that will relate the measured data to a correct physiological measurement. It is very difficult to both measure and account for all of the different variables that can affect a particular measurement. For example, while testing a patient for SpHb changes, the patient's perfusion index (PI) can change. Attempting to correlate all of the PI changes and accurately account for them while measuring changes in SpHb is extremely difficult, expensive, and time-consuming, as a large amount of data is often required. Moreover, such inconsistent testing leads to less accurate and precise results, particularly at extreme measurements. Even when a large amount of data is available, it may still be necessary to measure the various variables separately and then adjust or re-compute the desired measurement in real time to account for the variables.

The present disclosure provides a solution that allows for a measurement calibration which requires significantly less data and is much easier to implement than previous methods. Moreover, the present disclosure provides a calibration method that is more robust, particularly at extreme measurements. The present disclosure will be described with respect to correcting SpHb for PI changes, but it is to be understood that the methods described herein can be applied to other measurements as well.

Specifically, the present disclosure provides a technique for isolating changes due to a single variable at a time and then generating a robust calibration for the desired parameter. Any number of variables can be accounted for separately. Accounting for the effects of a single variable at a given time provides the quickest and least intensive solution.

In an embodiment, SpHb measurements are made impervious to interference from unrelated physiological changes. The present disclosure takes advantage of the knowledge that the optics used to obtain the SpHb measurements can be approximated to be linear in the regions of interest. This makes it possible to map ratio measurements into an orthogonal vector, making SpHb measurements uncorrelated with the effects due to PI changes and/or other variables that affect SpHb measurements. This essentially takes away any affect that changes in PI would make on SpHb measurements and thus removes the necessity of separately measuring and accounting for PI and other variables in SpHb measurements during patient measurements. Thus, the SpHb measurements become more robust.

In a particular example, a living patient can be cooled, and then warmed, to measure the effects of PI on SpHb. As the patient's body temperature rises, the effects of PI are measured with respect to internal measurements relevant to SpHb. For example, as the PI increases, the ratios of absorption levels of different wavelengths obtained using the optical measurements are observed to change. These measurements are then used determine a mapping of ratios to SpHb measurements that is less affected by changes in PI while measuring SpHb.

Once the isolated measurements are complete, for example, once a sufficient amount of data is obtained through PI tests while holding other variables constant, the data is used to model the relationship between PI and some of the internal measurements that in turn affect the prediction of the desired parameter, for example SpHb. This relationship can be used to adjust the measurement of the desired parameter. This calibration information can further be used to calibrate a physiological measurement system to obtain measurements for SpHb that are decorrelated from other variables.

Example Physiological Measurement System

FIG. 1 illustrates an embodiment of a physiological measurement system 100. The physiological measurement system 100 can measure various physiological parameters, such as $SpO_2$, desaturation, pulse rate (PR), perfusion index (PI), total hemoglobin (SpHb), HbCO, and HbMet. Further, the physiological measurement system 100 can calculate and display values of physiological parameters, as well as fluctuations, trends, or other indications of changes in the physiological parameters measured by the physiological management system 100. In some embodiments, the physiological measurement system 100 can provide displays, alarms, or controls responsive to physiological parameters (such as SpHb, PI, or other parameters) or changes thereto that can affect the treatment of the patient whose physiological parameters are being measured.

As shown in FIG. 1, the physiological measurement system 100 includes a patient monitor 102 and a sensor 106. The sensor 106 attaches to a patient's tissue site 1 and includes an array of one or more emitters 122 capable of irradiating the tissue site 1 with at least two known wavelengths of light, such as red and infrared (IR) wavelengths commonly utilized in pulse oximeters. The emitters 122 can be configured to emit other wavelengths as well, and these wavelengths can be emitted in addition to or instead of the red and IR wavelengths discussed above. For example, the emitters 122 can be configured to emit at least three known wavelengths of light, which can include a red wavelength, an IR wavelength, and a third wavelength. The third wavelength can itself be a red or IR wavelength, or can be any other wavelength selected as desired. In some embodiments, each individual emitter of the emitters 122 is configured to emit a unique wavelength. In other embodiments, an emitter of the emitters 122 can be configured to emit multiple wavelengths, either simultaneously or one at a time. In some embodiments, the emitters 122 are arranged in rows and/or columns of individual emitters, with each individual emitter being configured to emit light in response to an electrical drive signal. Further information pertaining to the emitters 122 can be found in U.S. Pat. No. 7,764,982, titled "MULTIPLE WAVELENGTH SENSOR EMITTERS," filed on Mar. 1, 2006, and issued on Jul. 27, 2010. The disclosure of this patent was previously incorporated by reference in its entirety.

The light emitted by the emitters 122 is attenuated by the tissue site 1 as it passes through to the one or more detectors 124, which can detect the light emitted by the emitters 122 and attenuated by the tissue site 1. In some embodiments, an individual detector is provided for each different wavelength emitted by the emitters 122. For example, if the emitters 122 are configured to emit a red wavelength, an IR wavelength, and a third wavelength, three detectors can be provided: one to detect the red wavelength, one to detect the IR wavelength, and one to detect the third wavelength. In other embodiments, a single detector of the detectors 124 can detect multiple wavelengths of light.

With continued reference to FIG. 1, the patient monitor 102 communicates with the sensor 106 to receive one or more intensity signals indicative of one or more physiological parameters and displays the parameter values. The drivers 110 can convert digital control signals into analog drive signals capable of driving sensor emitters 122. A front-end 112 can convert composite analog intensity signal(s) from light sensitive detector(s) 124 into digital data 142 to be provided to the digital signal processor (DSP) 140. The digital data 142 includes channels corresponding to each emitter wavelength, such as a red channel, an IR channel, and a channel for a third wavelength. The digital data 142 can be representative of a change in the absorption of particular wavelengths of light as a function of the changes in body tissue resulting from pulsing blood and/or from changing amounts of hemoglobin in the blood.

The DSP 140 can include a wide variety of data and/or signal processors capable of executing programs for determining physiological parameters from input data. In an embodiment, the calibration processes 130 can be implemented as a computer system that includes software, firmware, or other form of code or instructions, or logic or other hardware, or a combination of the above. In some embodiments, the DSP 140 can partially or wholly implement one or more calibration processes 130, as described further with respect to FIG. 2, FIG. 3, and FIG. 4. The DSP 140 can, for example, be configured to determine calibration information, and can further use the calibration information to calibrate the sensor 106 to obtain a decorrelated measurement of the selected physiological parameter.

Figure 2:
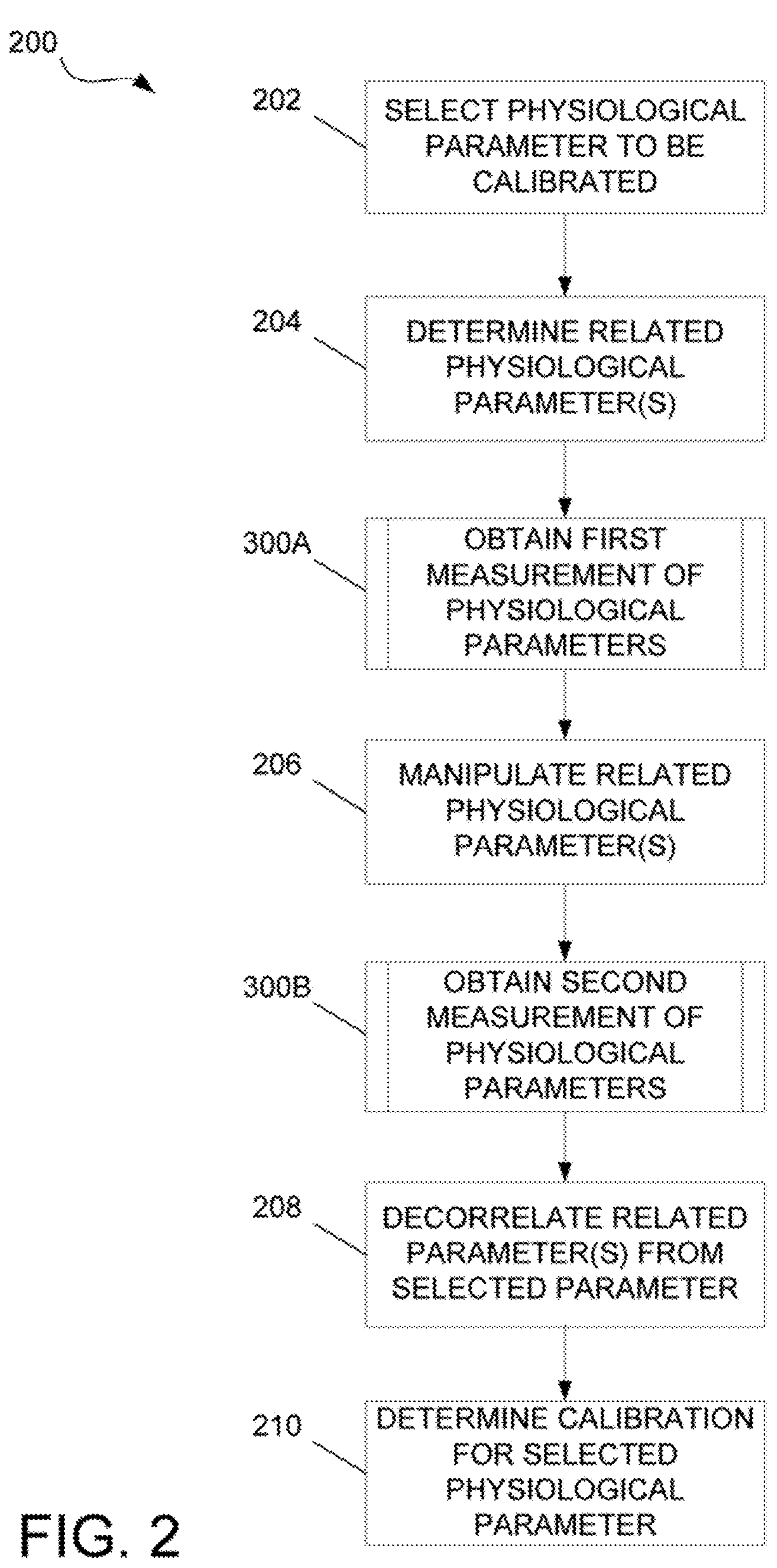
FIG. 2 is a flowchart illustrating an example technique for calibrating a physiological measurement system.
Figure 3:
FIG. 3 is a flowchart illustrating an example technique for obtaining measurements of physiological parameters using the physiological measurement system of FIG. 1.
Figure 3:
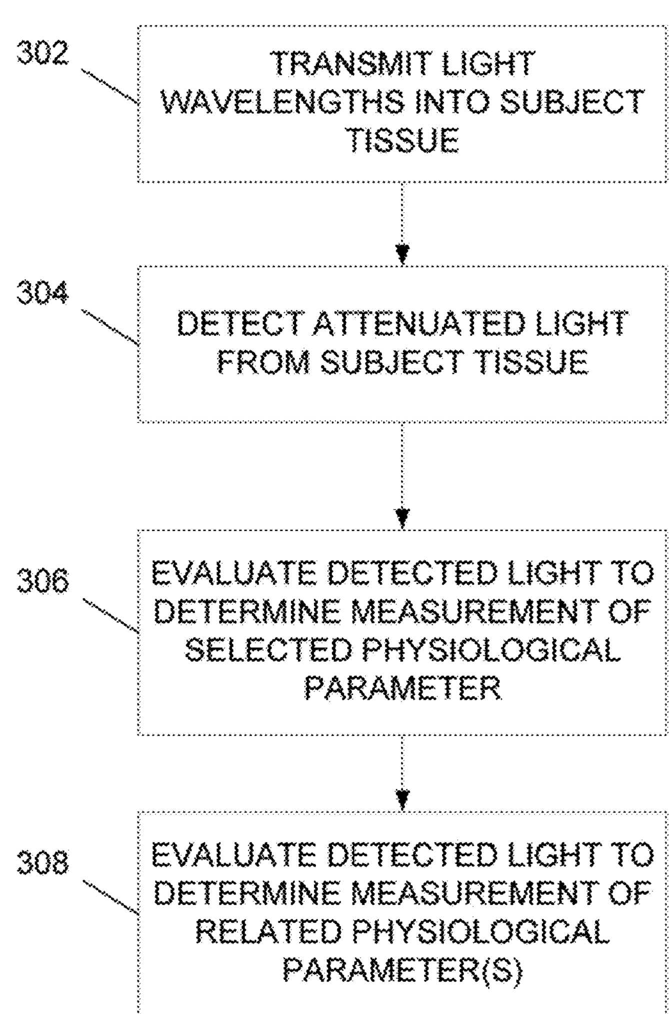
Figure 4:
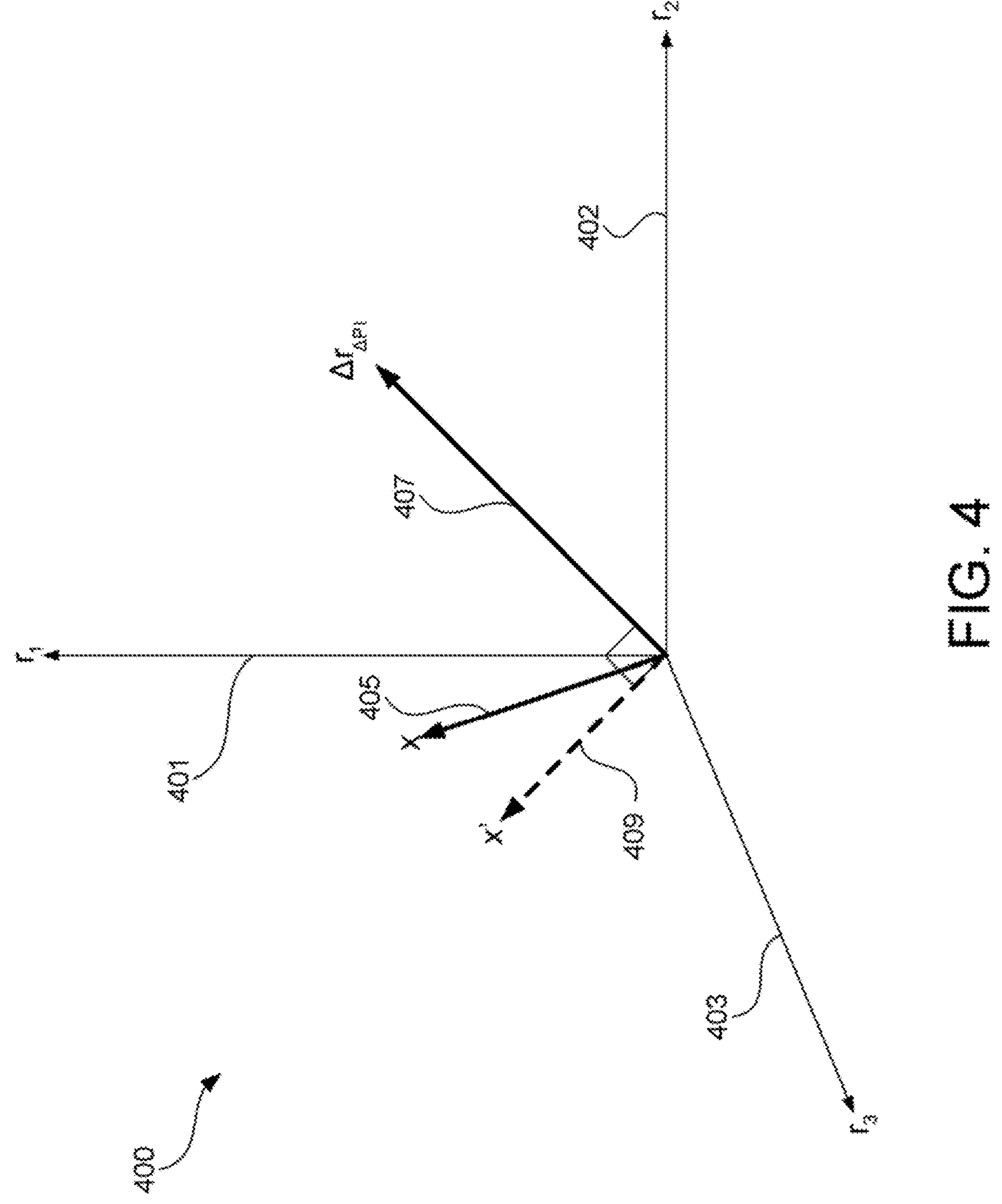
FIG. 4 is a graph illustrating example mathematical relationships which can be analyzed to implement the example technique shown in FIG. 2.

In other embodiments, the calibration processes 130 are implemented as a computer system that is separate from the physiological measurement system 100, as also described further with respect to FIG. 2, FIG. 3, and FIG. 4. For example, the computer system can be provided with data corresponding to a plurality of physiological measurements, without necessarily being capable of taking physiological measurements of a living patient. The computer system can determine calibration information from the plurality of measurements, and provide the calibration information to a physiological measurement system 100 that includes the DSP 140. The DSP 140 can use the provided calibration information to calibrate the sensor 106, substantially as discussed above.

Further shown in FIG. 1, the instrument manager 160 can comprise one or more microcontrollers controlling system management, such as monitoring the activity of the DSP 140. One or more output devices 180 include displays 182, alarms 184 and controls 186. The displays 182 can present information regarding one or more physiological parameter measurements in any of a variety of ways. For example, the displays 182 can present numerical information, such as readouts; or can present graphical information, such as trends and bar graphs. The displays 182 can include one or more LED screens, LCD screens, CRT displays, dot matrix displays, touchscreens, or any other kind of display hardware known in the art. The displays 182 can also include LEDs of various colors that can signify the magnitude of a physiological parameter measurement. Alarms 184 can be visual or audible alerts that can indicate any of a variety of conditions that can be pertinent to a patient's physiological parameters. For example, the alarms 184 can indicate that a particular physiological parameter is, for example, above or below a threshold. The alarms 184 can also indicate that a particular physiological parameter has changed or is trending in a direction that is pertinent to a patient's care. Controls 186 can be inputs to medical equipment, such as drug administration devices, ventilators and fluid IVs, so as to control the amount of administered drugs, ventilator settings or the amount of fluids infused to a patient. The instrument manager 160 can also include an input/output (I/O) port 168 that provides a user and/or device interface for communicating with the monitor 102. User input devices 188 can include a keypad, touch screen, pointing device, voice recognition device, network and computer, among other examples. In an embodiment, the I/O port 168 provides initialization settings for physiological measurement calibrations, as described below. The monitor 102 can also store or display historical or trending data related to SpHb, PI, and other measured parameters or combinations of measured parameters.

Example Calibration Technique

FIG. 2 depicts an example technique 200 by which a calibration can be determined for a physiological parameter measurement. This example technique 200 can be implemented to calibrate the physiological measurement system 100 of FIG. 1 to obtain a robust measurement, such that the measurement of a selected physiological parameter is not affected by a measurement of related physiological parameter(s). Other physiological measurement systems can also be calibrated using the technique described herein.

At block 202, a physiological parameter for which measurements are to be calibrated is selected. Generally described, a physiological parameter can include any quantifiable aspect of a living patient that can be measured. The selection of the physiological parameter can vary based on the capabilities of the physiological measurement system. For illustrative purposes, specific reference is made herein to calibrating a physiological measurement system to facilitate obtaining a robust SpHb measurement. However, calibrations can be determined for other physiological parameters as well, such that robust measurements of those parameters can be obtained. Such physiological parameters can include, for example, $SpO_2$, desaturation, pulse rate (PR), perfusion index (PI), HbCO, and HbMet. Calibrations can be determined for still other selected physiological parameters.

At block 204, one or more physiological parameters related to the physiological parameter selected in block 202 are determined. A related physiological parameter can include any parameter that affects the observation of the selected physiological parameter, such that a change in the related physiological parameter can cause a change in the observation of the selected physiological parameter, or vice versa. In a particular example provided for illustrative purposes, if a living patient's SpHb is the physiological parameter selected in block 202, a related physiological parameter can be the living patient's perfusion index (PI). In another embodiment, if the living patient's SpHb is the physiological parameter selected in block 202, the related physiological parameter can be the living patient's desaturation. Still other related parameters are possible. Additionally, in some embodiments, multiple physiological parameters are related to the selected physiological parameter. Returning to the previous example, if the living patient's SpHb is the physiological parameter selected in block 202, both desaturation and PI can be related physiological parameters.

At block 300A, a first measurement is obtained of the selected physiological parameter and of the one or more related physiological parameters. This measurement can be obtained, for example, by the sensor 106, and processed by the DSP 140 as shown in the physiological management system 100 of FIG. 1. An example technique 300 for obtaining a physiological measurement is shown in FIG. 3. Other techniques for obtaining a measurement of physiological parameters are possible.

At block 206, the one or more related physiological parameters are manipulated. In some embodiments, only one related physiological parameter is manipulated. In embodiments in which multiple related physiological parameters have been identified in block 204, one, some, or all of the related physiological parameters can be manipulated. The selected physiological parameter and other related physiological parameters can be held constant while a particular related physiological parameter is manipulated.

In a particular, non-limiting, example, the selected physiological parameter can be a non-invasive total hemoglobin parameter (SpHb) of a living patient, while the related physiological parameter can be a perfusion index (PI) of the living patient. Accordingly, the PI of the living patient can be manipulated in block 206. In an embodiment, during the measurement process, SpHb and all other parameters and variables are held constant while PI is manipulated. PI, in particular, is very difficult to manipulate as it relates to how constricted a patient's blood vessels are. In an embodiment, PI is manipulated by lowering the whole body temperature and then slowly raising the test patient's body temperature. As the patient's body temperature rises, the PI will increase. This is because when the patient is cold, the natural body reaction is to constrain blood vessels in order to keep blood in the body's core and thus keep the vital organs warm. As the body temperature increases, the blood vessels open up and allow more blood to flow in the extremities, thus increasing PI.

Accordingly, in an embodiment, a patient's temperature is lowered using alcohol sprayed on a patient's foot or feet. In an embodiment, the patient is placed in an environment (such as a room) having a particular known temperature. For example, the patient can be placed in an environment that is at room temperature. The patient may then be warmed up. In another example, the patient can be placed in an environment having a relatively cool temperature and allowed to acclimatize to the relatively cool temperature. In an embodiment, the patient's body temperature is increased by applying a body warmer to the patient. A body warmer can include a body blanket warmer, electric blanket, blankets, surgical warming blankets, whole body warmers, heat lamps, space warmers, or any other system for warming the patient.

Of course, other physiological parameters related to SpHb can be individually manipulated as is well known in the art. For example, similar isolated measurements can be made to account for desaturations. This can be done for example, by having a patient hold his or her breath. Other variables can also be isolated and manipulated as well.

At block 300B, a second measurement is obtained of the selected physiological parameter and of the one or more related physiological parameters. This measurement can be obtained, for example, by the sensor 106, and processed by the DSP 140 as shown in the physiological management system 100 of FIG. 1. Again, an example technique 300 for obtaining a physiological measurement is shown in FIG. 3. Other techniques for obtaining a measurement of physiological parameters are possible. Further, the first measurement obtained at block 300A and the second measurement obtained at block 300B can be obtained by the same technique or by different techniques.

In block 208, the selected physiological parameter and the one or more related physiological parameters are decorrelated from one another. In one embodiment, decorrelating the selected physiological parameter and the one or more related physiological parameters includes determining a vector for the selected physiological parameter that is orthogonal to one or more vectors for the one or more related physiological parameters, as discussed further herein with respect to FIG. 4. A calibration function can be minimized to identify the vector. In some embodiments, the calibration function is based on one or more weights assigned to ratios of wavelengths of attenuated light detected by the sensor 106 of the physiological measurement system 100, and thus the vector can include the weights of the ratios. If multiple related physiological parameters are to be decorrelated from the selected physiological parameter, a vector for the selected physiological parameter can be determined that is mutually orthogonal with respect to each of the vectors of the related parameters. Once the vector for the selected physiological parameter is determined, it can be included in calibration information to facilitate calibrating a sensor 106, such that the calibrated sensor is configured to obtain a decorrelated measurement.

Finally, in block 210, a calibration can be determined for the selected physiological parameter, based on the decorrelation performed in block 208. The calibration can be used to calibrate a physiological measurement system 100 to obtain a decorrelated measurement of the selected physiological parameter that reduces or eliminates the effects of the one or more related physiological parameters. In some embodiments, this calibration can be provided as calibration information, which can be processed by the DSP 140 of the physiological measurement system to enable the sensor 106 to obtain a decorrelated measurement of the selected physiological parameter.

Many variations of the example technique 200 are possible. In one embodiment, the related physiological parameter(s) are manipulated more than twice, and thus more than two measurements can be taken and used to decorrelate the selected physiological parameter and the selected physiological parameters. Further, measurements need not be taken from the same living patient. Measurements from different living patients can be obtained, without necessarily manipulating the physiological parameters of the different living patients. Still other variations on the calibration technique 200 are possible.

Example Physiological Parameter Measurement Technique

FIG. 3 depicts an example technique 300 for obtaining a physiological parameter measurement from a living patient. This example technique 300 can be implemented with the physiological measurement system 100 of FIG. 1, though other physiological measurement systems can be used to obtain physiological parameter measurements as well. Likewise, techniques other than the technique 300 illustrated in FIG. 3 can be used to obtain a physiological parameter measurement. The technique for obtaining a physiological parameter measurement can vary based on the parameter to be measured.

At block 302, light is emitted by the emitters 122, such that the emitted light impinges upon a living patient's tissue at the tissue site 1. As discussed above, in some embodiments, the light wavelengths comprise at least two wavelengths of light, which can include light of a red wavelength and light of an infrared wavelength. In some embodiments, the light wavelengths comprise at least three wavelengths of light, which can include light of a red wavelength, light of an infrared wavelength, and light of a third wavelength, which can be selected as desired.

The tissue at the tissue site 1 attenuates the light emitted by the emitters 122. Thus, in block 304, the attenuated light is detected by the detectors 124 after it emerges from the tissue at tissue site 1. The intensity of each wavelength of light can be determined by the detectors 124 and converted into digital data for processing by the digital signal processor 140, as discussed above with respect to FIG. 1.

At block 306, the detected light can be evaluated to determine a measurement (e.g., a measured value) of the selected physiological parameter. In some embodiments, the selected physiological parameter is a non-invasive total hemoglobin parameter (SpHb) of the living patient. Since hemoglobin causes different degrees of attenuation for different wavelengths of light, the degree to which each wavelength of light is attenuated can be evaluated to determine the SpHb measurement. For example, if three wavelengths of light are emitted by the emitters 122, the attenuation ratio (e.g., the intensity of the attenuated light detected by the detectors 124 divided by the intensity of the unattenuated light emitted by the emitters 122) for each wavelength can be used to determine the SpHb measurement. For example, each wavelength's attenuation ratio can be weighted, and the weighted ratios can be summed to determine the SpHb measurement. Still other techniques for determining an SpHb measurement based on the detected light are possible.

At block 308, the detected light is evaluated to determine a measurement (e.g., a measured value) of one or more related physiological parameters. In some embodiments, the one or more physiological parameters include a perfusion index (PI) of the living patient. More information pertaining to the measurement of PI can be found in U.S. patent application Ser. No. 12/011,011, entitled "PERFUSION TREND INDICATOR," filed on Jan. 22, 2008, and published as U.S. Patent Application Publication No. 2008/0221464 on Sep. 11, 2008. The disclosure of this application was also previously incorporated by reference above and is also provided as an appendix to this application.

Other parameters can be included in the one or more physiological parameters to be measured. For example, desaturation, pulse rate, tissue temperature, HbMet, HbCO, $SpO_2$, and the like can be measured as desired. More information on determining physiological parameters can be found at least in U.S. Pat. No. 8,130,105, titled "NON-INVASIVE MULTI-PARAMETER PATIENT MONITOR," filed on Mar. 1, 2006, and issued on Mar. 6, 2012. The disclosure of this patent was previously incorporated by reference in its entirety.

Example Decorrelation

Turning now to FIG. 4, a graph 400 is shown to illustrate example mathematical relationships of the present disclosure. The graph has axes $r_1$ 401, $r_2$ 402, and $r_3$ 403. The coordinates $r_1$, $r_2$ and $r_3$ represent ratios of wavelengths obtained from a noninvasive optical sensor 106 having at least three wavelengths, substantially as discussed above with respect to FIG. 1. Of course, more ratios and more wavelengths can be used and an n-dimensional graph can be generated accordingly. Each axis corresponds to a linear calibration fit for SpHb. That is, SpHb is found using the following equation:

$$SpHb = x_1 r_1 + x_2 r_2 + x_3 r_3 \quad \text{(Eq. 1)}$$

where $x_1$, $x_2$ and $x_3$ are weights. The original calibration fit for SpHb is illustrated by the vector 405, labeled as X.

The data obtained by isolating and manipulating PI is also illustrated in graph 400 as vector 407, labeled as $\Delta r_{\Delta PI}$, or in other words, the change in the ratios based on the change in PI. The calibration of SpHb based on PI can be found by determining a set of x values (weights) that minimizes a calibration function based on the first measurement and the second measurement of SpHb. In one embodiment, the calibration function is given by $$_{min} f(x) = \|RX - t\|^2 + \alpha\|CX\|^2 \quad \text{(Eq. 2)}$$

where $$R = \begin{bmatrix} r1_{measurement\text{-}1} & r2_{measurement\text{-}1} & r3_{measurement1} \\ r1_{measurement2} & r2_{measurement2} & r3_{measurement2} \end{bmatrix} \quad \text{(Eq. 3)}$$

$$X = \begin{bmatrix} x_1 \\ x_2 \\ x_3 \end{bmatrix} \quad \text{(Eq. 4)}$$

$$C = [\,\Delta r_{1\Delta PI} \;\; \Delta r_{2\Delta PI} \;\; \Delta r_{3\Delta PI}\,] \quad \text{(Eq. 5)}$$

$$t = \begin{bmatrix} tHb_1 \\ tHb_2 \end{bmatrix} \quad \text{(Eq. 6)}$$

and where $tHb_1$ and $tHb_2$ are reference total hemoglobin measurements. For example, $tHb_1$ and $tHb_2$ can be obtained by drawing a sample of the patient's blood and using accepted or "gold standard" measurement methods to determine a total hemoglobin value as known in the art. In particular, non-limiting examples, the tHb measurements can be obtained via spectrophotometric analysis or conductometric analysis of the patient's blood sample. The constant $\alpha$ is a non-zero positive real number, which can be selected as desired. A higher $\alpha$ may provide greater decorrelation, but may introduce measurement errors. A lower $\alpha$ may provide a lower measurement error, but may also increase the correlation between SpHb and PI.

Once a set of x values are determined that minimizes the calibration function f(x) in Eq. 1, they can be plotted as vector 409, labeled as X'. The set of X' values found using Eq. 1 is then used to not only predict SpHb, but also make it insensitive to changes in PI. This vector can be included in calibration information and used to calibrate a sensor 106 and/or DSP 140 of a physiological measurement system 100 to obtain decorrelated measurements of SpHb.

This same process can also be applied to any related physiological parameters that can affect a measurement of a selected physiological parameter. Moreover, multiple related physiological parameters can be decorrelated from the selected physiological parameter. For example, SpHb can be decorrelated from both PI and desaturation. Once sufficient data is obtained, the x values can again be mapped to a new orthogonal vector or taken into account in Eq. 1 to find a mutually orthogonal vector to both the effects of PI and desaturation. Such a process can be applied to any number of variables or to other desired parameters.

Additionally, it will be recognized that other techniques can be used to decorrelate the selected physiological parameter from its related physiological parameters. For example, multiple regression analysis, conjoint analysis, and other techniques can be used to determine the effects of related physiological parameters on the selected physiological parameter, and to generate calibration information such that a decorrelated measurement of the selected physiological parameter can be obtained. Still other techniques are possible.

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor can also include primarily analog components. For example, any of the signal processing algorithms described herein can be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A physiological monitoring system comprising:

a sensor including a plurality of light emitters configured to shine light of known wavelengths into tissue of a patient and at least two detectors configured to detect the light after the light has been attenuated by the tissue, wherein an individual detector is provided for each different wavelength emitted by the plurality of light emitters; and a processor in communication with the sensor, the processor configured to receive the detected light and determine a non-invasive total hemoglobin measurement (SpHb) based on calibration information which decorrelates SpHb measurements from changes in a perfusion index of the patient.

2. The physiological monitoring system of claim 1, wherein the calibration information is determined based on empirical data.

3. The physiological monitoring system of claim 2, wherein the empirical data is obtained from a cross-section of patients.

4. The physiological monitoring system of claim 3, wherein the perfusion index of the cross-section of patients is manipulated by warming the patients.

5. The physiological monitoring system of claim 3, wherein the perfusion index of the cross-section of patients is manipulated by cooling the patients.

6. A method for physiological parameter measurement calibration, the method comprising:

shining light of a plurality of wavelengths into a patient's tissue;

detecting the light after the light has been attenuated by the patient's tissue;

obtaining a first measurement of the patient's SpHb and a related physiological parameter, wherein the first measurement is based at least in part on one or more attenuation ratios of absorption energies associated with each known wavelength of the light;

obtaining a second measurement of the patient's SpHb and the related physiological parameter, wherein the patient's SpHb measurement is substantially the same and wherein the related physiological parameter is manipulated and the patient's SpHb is held the same;

combining the first measurement and the second measurement with similar measurements from other patients to determine calibration information useful for decorrelating SpHb measurements from related physiological parameters; and based on the calibration information, configuring a physiological parameter measurement system to obtain a decorrelated SpHb measurement.

7. The method of claim 6, wherein the related physiological parameter is the patient's perfusion index.

8. The method of claim 7, wherein the patient's perfusion index is manipulated by manipulating the patient's body temperature.

9. The method of claim 8, wherein the patient's body temperature is manipulated by spraying alcohol on the patient.

10. The method of claim 8, wherein the patient's body temperature is manipulated by a body warmer applied to the patient.

11. The method of claim 9, wherein the patient's body temperature is manipulated by placing the patient in an environment having a known temperature.

12. The method of claim 6, wherein the related physiological parameter is the patient's desaturation.

13. The method of claim 12, wherein the patient's desaturation is manipulated by the patient holding his or her breath.

14. Non-transitory computer storage having stored thereon a system configured to execute in one or more processors, the system comprising a calibration module configured to:

obtain a plurality of correlated measurements, each correlated measurement comprising a measurement of a selected physiological parameter and a measurement of a related physiological parameter;

based on the plurality of correlated measurements, decorrelate the selected physiological parameter and the related physiological parameter; and based on the decorrelation of the selected physiological parameter and the related physiological parameter, determine calibration information;

wherein the calibration information facilitates obtaining a decorrelated measurement of the selected physiological parameter;

wherein the calibration module is further configured to use the calibration information to calibrate a physiological parameter measurement system to obtain the decorrelated measurement of the selected physiological parameter;

wherein the physiological parameter measurement system includes a sensor having a plurality of light emitters configured to shine light of known wavelengths into tissue of a patient and at least two detectors configured to detect the light after attenuation by the tissue, wherein an individual detector is provided for each different wavelength emitted by the plurality of light emitters.

15. The non-transitory computer storage of claim 14, wherein the calibration module is further configured to use the calibration information to calibrate the physiological parameter measurement system to obtain the decorrelated measurement of the selected physiological parameter.

16. The non-transitory computer storage of claim 14, wherein the calibration module is configured to decorrelate the selected physiological parameter and the related physiological parameter by minimizing a value of a correlation function that relates the selected physiological parameter and the first related physiological parameter.

17. The non-transitory computer storage of claim 14, wherein:

each of the plurality of correlated measurements further comprises a measurement of a second related physiological parameter; and the calibration module is further configured to decorrelate the selected physiological parameter, the first related physiological parameter, and the second related physiological parameter.

18. The non-transitory computer storage of claim 17, wherein the calibration module is configured to decorrelate the selected physiological parameter, the first related physiological parameter, and the second related physiological parameter by:

determining a vector that represents a change in the selected physiological parameter with respect to a change in the related physiological parameter;

determining a second vector that represents a change in the selected physiological parameter with respect to a change in the second related physiological parameter; and determining a third vector that is orthogonal to both the first vector and the second vector;

wherein the calibration information comprises the third vector.

19. The non-transitory computer storage of claim 17, wherein:

the selected physiological parameter is SpHb;

the related physiological parameter is perfusion index; and the second related physiological parameter is desaturation.

* * * * *